(12) United States Patent
Shen et al.

(10) Patent No.: US 9,326,743 B2
(45) Date of Patent: May 3, 2016

(54) MULTI-ENERGY CT IMAGING SYSTEM AND IMAGING METHOD

(71) Applicants: TSINGHUA UNIVERSITY, Beijing (CN); NUCTECH COMPANY LIMITED, Beijing (CN)

(72) Inventors: Le Shen, Beijing (CN); Yuxiang Xing, Beijing (CN); Qi Shen, Beijing (CN); Meng Cao, Beijing (CN); Li Zhang, Beijing (CN); Zhiqiang Chen, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 247 days.

(21) Appl. No.: 14/135,023

(22) Filed: Dec. 19, 2013

(65) Prior Publication Data

US 2014/0185741 A1    Jul. 3, 2014

(30) Foreign Application Priority Data

Dec. 31, 2012  (CN) .......................... 2012 1 0589336
Jan. 10, 2013  (CN) .......................... 2013 1 0008543

(51) Int. Cl.
| | | |
|---|---|---|
| A61B 6/00 | (2006.01) | |
| G01N 23/04 | (2006.01) | |
| G01V 5/00 | (2006.01) | |
| A61B 6/02 | (2006.01) | |
| A61B 5/00 | (2006.01) | |

(52) U.S. Cl.
CPC . *A61B 6/482* (2013.01); *A61B 6/54* (2013.01); *G01N 23/046* (2013.01); *G01V 5/005* (2013.01); *A61B 5/4869* (2013.01); *A61B 6/027* (2013.01); *A61B 6/5205* (2013.01); *G01N 2223/419* (2013.01)

(58) Field of Classification Search
CPC .......... A61B 6/482; A61B 6/54; A61B 6/027; A61B 6/5205; A61B 5/4869; G01V 5/005; G01N 23/046
USPC .......................... 378/4–20, 57, 111, 114, 116
See application file for complete search history.

(56) References Cited

U.S. PATENT DOCUMENTS

| | | | |
|---|---|---|---|
| 5,661,774 A | 8/1997 | Gordon et al. | |
| 6,236,709 B1 | 5/2001 | Perry | |
| 7,209,537 B2 * | 4/2007 | Popescu ................. | A61B 6/032 378/108 |
| 7,945,013 B2 * | 5/2011 | Goto .................... | A61B 5/4869 378/16 |
| 7,949,088 B2 * | 5/2011 | Nishide ................. | A61B 6/032 378/16 |

(Continued)

FOREIGN PATENT DOCUMENTS

| | | |
|---|---|---|
| CN | 1502309 A | 6/2004 |
| CN | 1509686 | 7/2004 |

(Continued)

OTHER PUBLICATIONS

Torikoshi, Masami, et al., "Electron density measurement with dual-energy x-ray CT using synchrotron radiation," Phys. Med. Biol. 48 (2003) pp. 273-685.

(Continued)

*Primary Examiner* — Courtney Thomas
(74) *Attorney, Agent, or Firm* — Casimir Jones, SC

(57) ABSTRACT

The present invention relates to a Computed Tomography (CT) imaging system, in particular to a multi-energy CT imaging system and imaging method.

6 Claims, 3 Drawing Sheets

(56) References Cited

U.S. PATENT DOCUMENTS

| | | |
|---|---|---|
| 2004/0102688 A1 | 5/2004 | Walker |
| 2007/0237288 A1 | 10/2007 | Tkaczyk |
| 2008/0273666 A1 | 11/2008 | Walter |
| 2009/0028288 A1 | 1/2009 | Horiuchi |
| 2009/0092219 A1 | 4/2009 | Wu |
| 2009/0097611 A1 | 4/2009 | Nishide |
| 2009/0129539 A1 | 5/2009 | Licato |
| 2010/0189212 A1 | 7/2010 | Zou |

FOREIGN PATENT DOCUMENTS

| | | |
|---|---|---|
| CN | 1765327 A | 5/2006 |
| CN | 1994230 | 7/2007 |
| CN | 101028199 | 9/2007 |
| CN | 101772324 A | 7/2010 |
| CN | 203149136 | 8/2013 |
| JP | 2008142390 | 6/2008 |
| JP | 2011005018 | 1/2011 |

OTHER PUBLICATIONS

Tsunoo, T., et al., "Measurement of electron density and effective atomic number using dual-energy x-ray CT," pp. 3764-3768, Oct. 16-22, 2004, Published in Nuclear Science Symposium Conference Record (2004) IEEE.

Gao et al. "Dual energy CT reconstruction associated with total variation minimization" Application Research of Computers, vol. 29, No. 3, Mar. 2012, pp. 1158-1161.

* cited by examiner

MULTI-ENERGY CT IMAGING SYSTEM AND IMAGING METHOD

CROSS-REFERENCE TO RELATED APPLICATION

The present application claims priority to pending Chinese Patent Application Nos. CN201310008543.3, filed Jan. 10, 2013, and CN 201210589336.7, filed Dec. 31, 2012, the contents of which are incorporated by reference in their entirety.

TECHNICAL FIELD

The present invention relates to a Computed Tomography (CT) imaging system, in particular to a multi-energy CT imaging system and imaging method. The present invention relates to multi-energy CT imaging system and imaging method. The multi-energy CT imaging system comprises: a stage for carrying the object to be inspected; voltage-regulatable X-ray generation device for emitting X-rays; a detector for receiving X-rays emitted from said X-ray generation device and penetrating said object to be inspected, and for outputting detection data; a rack having said X-ray generation device and said detector mounted thereon; and a data processing and control device for controlling said stage, said X-ray generation device, said detector and said rack, processing detected data, and during one rotation of scan of said X-ray generation device, evenly dividing the circular track of said X-ray generation device into angle intervals of a predetermined number according to the predetermined number of energies and setting a different high voltage of said X-ray generation device for each angle interval, and when said rack rotates from the current angle interval into a next angle interval, controlling said X-ray generation device to switch it to a voltage set in the next angle interval.

BACKGROUND OF THE INVENTION

The image contrast of a computed tomography (CT) image is closely related to spectrum distribution of the X-ray source used in the scan. The conventional CT uses a light source having spectrum distribution for imaging, sometimes, information blur might occur causing two different materials to be presented completely the same on the CT image; in contrast, the dual-energy CT uses two spectrums having different distributions to image objects, thus eliminating information blur caused by single energy spectrum. The dual-energy computed tomography (CT) technology takes advantage of the difference in attenuation of substance in different energies to obtain distribution information about multiple physical characteristics parameters of objects, for example, electron density distribution, equivalent atomic number distribution, and single energy attenuation image in multiple energies. Hence, the dual-energy CT can be used for correction of beam hardening of the conventional CT, obtaining clinical high-contrast spectrum images, detection of special and dangerous objects in industry and security check, etc. Compared to the conventional CT imaging technology, the dual-energy CT is significant to such application fields as medical diagnosis technologies, nondestructive testing and security check because of the breakthrough in imaging function it has made, so it has gained more and more widespread attention in recent years.

In addition, compared to the convention single energy CT technology, the dual-energy CT imaging technology can not only provide the attenuation coefficient and geometrical structure information of the object to be inspected, but also provide the material composition information thereof. Therefore, in the field of security check, the dual-energy CT technology can provide the electron density and effective atomic number information of the object to be inspected, thereby identifying dangerous substances. Moreover, in the field of medical treatment, the dual-energy CT can provide images of different tissue components, such as bone, soft tissue, contrast agent, etc.

The dual-energy CT system at present can mainly be implemented in three ways, i.e. dual-source dual-detector, single source double layer detector, fast energy switch. With respect to the dual-source dual-detector, as shown in FIG. 1, such a system consists of two sets of X-ray sources and detectors, i.e., the system comprises a high energy X-ray source 11, a high energy detector 12, a low energy X-ray source 21 and a low energy detector 22, and the high energy X-ray source 11 and high energy detector 12 intersect with the low energy X-ray source 21 and a low energy detector 22 at a angle of 90°. During data acquisition, these two sets of X-ray machines emit radiations of different energies (KVp), and the corresponding detectors collect data independently, so two groups of projection data, i.e. high energy projection data and low energy projection data, are obtained. However, the dual-source dual-detector system is very expensive, besides, it has high design requirements for the stability and strength of the mechanical structure of the rotating rack. In addition, with respect to the single source double layer detector, as shown in FIG. 2, in the design of such a system, a low energy filter and a detector (high energy detector in FIG. 2) are added behind the detector (low energy detector in FIG. 2) of the conventional single energy CT, thereby forming a dual-energy detector. When X-rays penetrate the first detector (low energy detector) and the filter, the low energy portion of X-rays is filtered out, and the high energy portion of X-rays reaches the second layer detector (high energy detector). Both detectors work simultaneously so as to collect two groups of projection data, i.e. low energy projection data and high energy projection data. However, the cost for such single source double layer detector is also high.

Moreover, with respect to the way of fast energy switch, such a system needs to use a special X-ray machine which can enable fast switch of high voltage and alternate emission of radiations of different energies (KVp). FIG. 3 is a schematic drawing of a dual-energy CT for realizing fast energy switch in a dual-energy CT system. As shown in FIG. 3(B), acquisition of high and low energy data can be realized by quickly switching the high voltage value of the X-ray machine. In this system, the rack rotates normally during scanning at a rotation speed of, for example, 0.5 s/rotation, with 1000 times of sampling being performed in each rotation, then the high voltage of the X-ray machine will be switched once in each sampling, and the detector will read data twice, high energy projection data in the first time and low energy projection data in the second time. At this time, the X-ray machine high voltage is switched 1000 times in one rotation, i.e. 0.5 second. However, in the fast energy switch system, a new type X-ray machine needs to be used, so said way of implementation has a high cost and is hard to be popularized and applied.

As mentioned above, the manufacturing costs for the above three types of dual-energy CTs are much higher than that of the conventional single energy CT, so they can hardly be popularized and used in common detections. In addition, the dual-energy CT cannot accurately reflect the true processes of the X-rays and the substance, so the result of reconstruction of some substance having characteristic absorption has poor accuracy, in contrast, the multi-energy CT is likely to solve this problem. Therefore, the multi-energy CT imaging system has gained extensive attention.

SUMMARY OF THE INVENTION

The present invention is made to solve the above-mentioned problem, and it aims at providing a multi-energy CT imaging system and imaging method, which can change the X-ray machine high voltage in several times during the scan in one rotation, thereby to image by multiple energies.

In addition, the present invention is made on the basis of the conventional single energy CT imaging system, and it can solve the above-mentioned problem without increasing the hardware cost.

Furthermore, as far as the hardware is concerned, the present invention uses substantially the same system design as the conventional single energy CT as well as the corresponding data processing and image reconstruction method to provide the multi-energy imaging function, so it has a low cost and can be widely used in fields like security check and medical diagnosis.

The present invention provides a multi-energy CT imaging system, characterized in that said system comprises:
a stage for carrying the object to be inspected;
a voltage-regulatable X-ray generation device for emitting X-rays for radiating said object to be inspected;
a detector for receiving X-rays emitted from said X-ray generation device and penetrating said object to be inspected, and for outputting detection data;
a rack having said X-ray generation device and said detector mounted thereon; and
a data processing and control device for controlling said stage, said X-ray generation device, said detector and said rack, processing detected data from said detector, and during one rotation of scan of said X-ray generation device, evenly dividing the circular track of said X-ray generation device into angle intervals of a predetermined number according to the predetermined number of energies and setting a different high voltage of said X-ray generation device for each angle interval, and when said rack rotates from the current angle interval into a next angle interval, controlling said X-ray generation device according to an instruction from said data processing and control device to switch said X-ray generation device to a voltage set in the next angle interval.

In addition, the present invention provides an imaging method of a multi-energy CT imaging system, characterized in that said imaging method includes the following steps:
(a) evenly dividing the circular track of the X-ray generation device of said multi-energy CT imaging system into angle intervals of a predetermined number according to the predetermined number of energy and setting a different high voltage of said X-ray generation device for each angle interval;
(b) said X-ray generation device rotating along the circular track and working in each angle interval at a high voltage set for said angle interval to emit X-rays to irradiate the object to be inspected;
(c) acquiring projection data of different energies using the detector of said multi-energy CT imaging system;
(d) obtaining line integral data of the projection data of said different energies using the data processing and control device of said multi-energy CT imaging system;
(e) splicing said line integral data of different energies one by one to obtain a complete line integral data covering 360°;
(f) reconstructing according to said complete line integral data to obtain a hybrid reconstruction result;

(g) using said hybrid reconstruction result as a priori image to respectively reconstruct each segment of incomplete data to obtain attenuation coefficient reconstruction results in different energies;
(h) obtaining decomposition coefficients from said attenuation coefficient reconstruction results and obtaining an atomic number distribution image and electron density distribution image using said decomposition coefficient.

In the imaging method of the multi-energy CT imaging system of the present invention, in step (a) the circular track is divided into N angle intervals and the line integral data in different energies obtained in step (d) are made to be $P_1$, $P_2, \ldots P_n$, and in step (f), reconstruction is performed using a common circular track filtering back projection method so as to make the obtained hybrid reconstruction result to be $f_0$, N and n being integers greater than or equal to 2; in step (g), an attenuation coefficient reconstruction result fi that satisfies the condition of $\|H_i f_i - p_i\|_2 < \epsilon$ is obtained by solving a minimized optimization problem arg min $G(f_i, f_0)$ having constraints, wherein, $G(f_i, f_0)$ is a function describing the difference between the priori image and the reconstruction result, $H_i$ is a projection operator in the $i^{th}$ energy, $\epsilon$ is a parameter related to measurement of data noise variance, i=1, 2, ..., n.

In the imaging method of the multi-energy CT imaging system of the present invention, in step (h), a decomposition coefficient is obtained using a post-processing base effect decomposition method, then said decomposition coefficient is used to obtain the atomic number distribution image and electron density distribution image.

In the imaging method of the multi-energy CT imaging system of the present invention, in step (h), a decomposition coefficient is obtained using post-processing base material decomposition method, then said decomposition coefficient is used to obtain the atomic number distribution image and electron density distribution image.

In the imaging method of the multi-energy CT imaging system of the present invention, in place of said step (h), there is such a step (j) as performing orthographic projection to the attenuation coefficient reconstruction result $f_i$ obtained in step (g) to obtain the completed projection data in which the scanning plane in different angles have been missing, then obtaining coefficients of different base functions by means of pre-processing, thus obtaining the atomic number distribution image and electron density distribution image.

According to the present invention, without changing the hardware design of the existing conventional single energy CT system, the circular track of the X-ray generation device is divided into predetermined angle intervals, and a predetermined high voltage of the X-ray generation device is set for each angle interval. By means of the reconstruction method of the present invention, a dual-energy imaging function is provided, thus extending the functionality of the conventional CT; moreover, compared to the existing dual-energy CT devices, it has a low cost.

DETAILED DESCRIPTION OF THE INVENTION

The embodiments of the present invention are described below with reference to the drawings.

Figure 1:
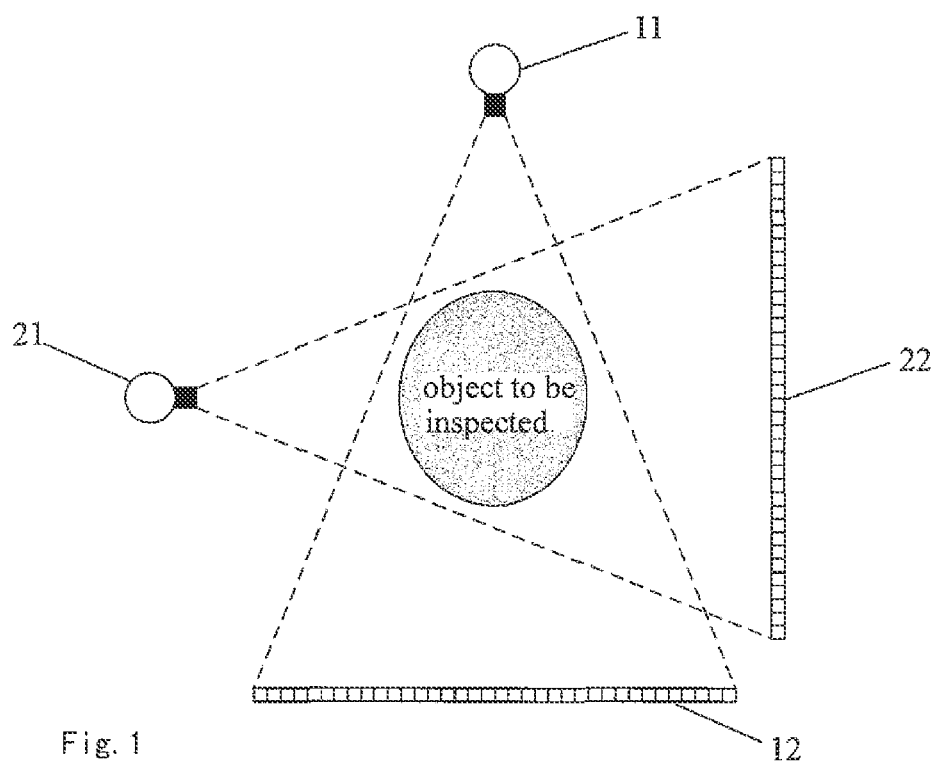
FIG. 1 is a schematic drawing of the dual-source dual-detector for implementing the dual-energy CT system.
Figure 2:
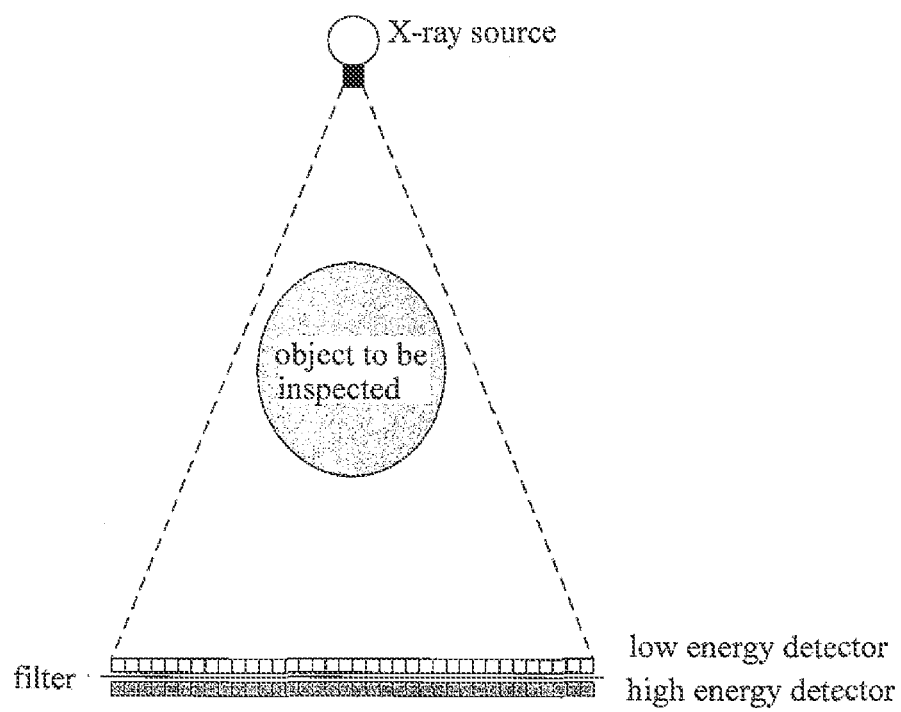
FIG. 2 is a schematic drawing of the single source double layer detector for implementing the dual-energy CT system.
Figure 3:
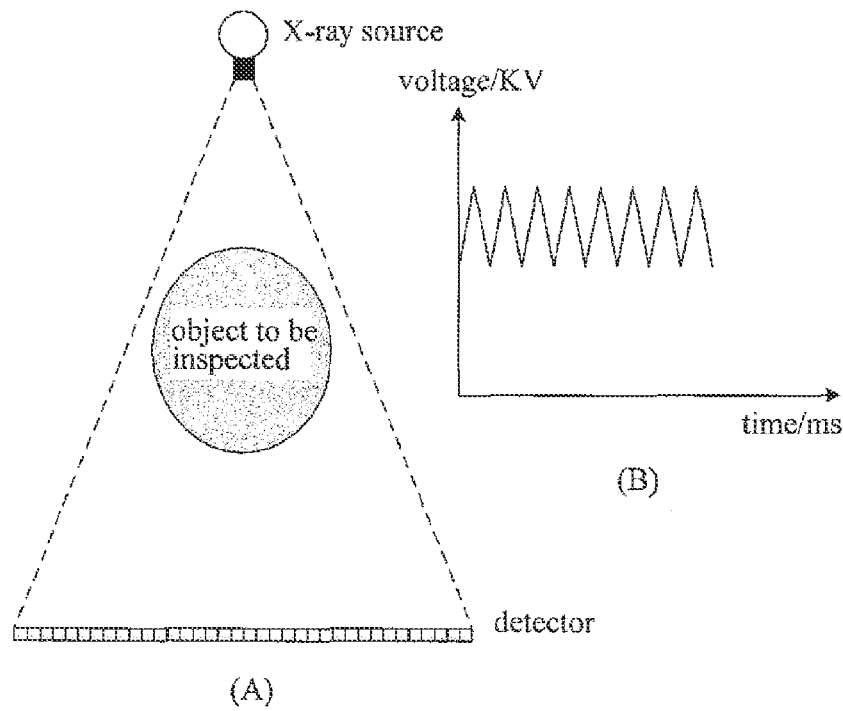
FIG. 3 is a schematic drawing of the dual-energy CT having fast energy switch for implementing the dual-energy CT system.
Figure 4:
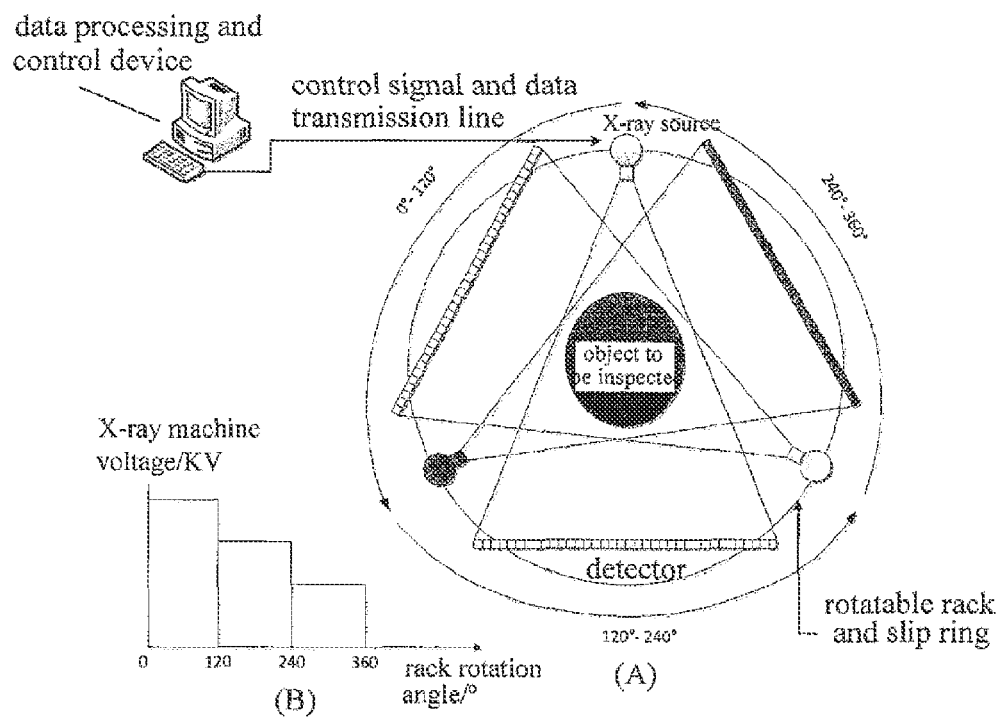
FIG. 4 is a schematic drawing of the multi-energy CT imaging system of the present invention.

FIG. 4 is a schematic drawing of the multi-energy CT imaging system of the present invention, wherein (A) is a schematic drawing of the system structure and the multi-energy scanning mode, and (B) is a diagram of the relationship between the rack rotation angle and the X-ray machine voltage. As shown in FIG. 4, the multi-energy CT imaging system of the present invention comprises a stage for carrying an object to be inspected (i.e. the object to be inspected in FIG. 4); a voltage-regulatable X-ray generation device (i.e. the X-ray source in FIG. 4) for emitting X-rays irradiating said object to be inspected; a detector for receiving X-rays emitted from said X-ray generation device and penetrating said object to be inspected, and for outputting detection data (e.g. projection data in different energies, etc.); a rack; a data processing and control device for controlling said stage, X-ray generation device, detector and rack, and processing said detection data from said detector.

In addition, the X-ray generation device used in the present invention is X-ray machine having a voltage regulation function, which can switch voltages under the control of the data processing and control device to emit X-rays of different energies. In addition, there is no particular limitation to the X-ray generation device used in the present invention, and any X-ray source can be used in the present invention as long as it can perform voltage switch under the control of the data processing and control device.

Moreover, the X-ray generation device and the detector are mounted on a ring-shape rack which can rotate continuously, besides, a slip ring mechanism is used to realize delivery of control signals to the X-ray generation device and transmission of data collected by the detector. In addition, it can also power the X-ray generation device (the function of the slip ring is similar to that of a generator brush). Furthermore, during operation of the CT imaging system, for example, the rack always rotates at a constant speed, if the plane on which the X-ray generation device rotates is plane XY (e.g. the paper plane herein), then the object to be inspected moves in a straight line on the conveyor belt along a Z-axis direction (i.e. moving perpendicular to the paper plane).

In addition, during the scanning in one rotation of the X-ray generation device, the data processing and control device evenly divides the circular track into a predetermined N (N being an integer greater than or equal to 2) angle intervals according to a predetermined number of energies, each angle interval being provided with a different high voltage of the X-ray generation device. When the rack rotates from the current angle interval into the next angle interval, the X-ray generation device is controlled according to instructions from the data processing and control device to switch the voltage to a voltage set in the next angle interval, thus X-rays of different energies are emitted.

The stage and rack respectively make the movement of rotation along the circular track and translation in a straight line or a combination thereof, thus realizing helical scan traces or circular scan traces. Specifically, as shown in FIG. 4(A), the stage in the present invention is a structure for holding the object. When the rack is rotating in a circle while the stage is still, or when the rack is still while the stage is rotating in a circle, scanning along a circular track can be realized, and these two ways are equivalent. Moreover, the helical movement can be decomposed into two sub-movements of circular movement in the plane XY and straight line movement along direction Z, and the stage and the rack each makes one of the sub-movements, then the sub-movements are combined to form the helical movement, for example, the stage makes the straight line movement and the rack makes the circular movement. It is also possible that the stage rotates while the rack translates, which is suitable for inspection of large objects, because translation of large objects require a very large ground space but rotation thereof is easier.

Furthermore, movements of the stage and the rack are relative movements, so the descriptions are made in the present invention according to the circular scanning trace obtained by fixing the stage and rotating the rack.

Furthermore, the data processing and control device consists of a computer, etc. for realizing control of the operation process of the multi-energy CT imaging system, such as mechanical rotation control, electrical control, safe interlocking control, etc. During the scanning in one rotation of the X-ray generation device, the circular track of the X-ray generation device is evenly divided into multiple angle intervals according to the number of energies needed, for example, the circular track is divided into two angle intervals of 180° under the condition of dual-energy, i.e. an angle interval of 0°~180° and an angle interval of 180°~360°. Under the condition of triple-energy (as shown in FIG. 4), the circular track is divided into three angle intervals of 120°, i.e. an angle interval of 0°~120°, an angle interval of 120°~240° and an angle interval of 240°~360°. Each angle interval is provided with a different X-ray machine high voltage, for example, in the case of dividing the circular track into two angle intervals of 180°, the X-ray machine high voltages are 120 KV and 80 KV, respectively. In addition, when the rack rotates from the current angle interval into the next, the data processing and control device sends instructions to control the X-ray machine to switch the X-ray machine voltage to the voltage set in the next angle interval. Since this single-step switching process can be performed quickly, it will not influence data acquisition.

In addition, the detector used in the present invention is a complete area array X-ray detector, but the detector is not limited to this, and any detector can be used as long as data detection can be performed. The multi-energy CT imaging system of the present invention also has a reading circuit, an acquisition triggering signal circuit and a data transmission circuit, which, together with the area array X-ray detector, form a data acquisition system for acquiring data.

The imaging method in the multi-energy CT imaging system of the present invention is described below.

The multi-energy CT imaging system of the present invention uses different energies to acquire data in the range of angle of the X-ray generation device scanning in one rotation along the circular track. For example, N energies are pre-selected (which are marked as $E_1, E_2, \ldots, E_n$), the circular track is evenly divided into N angle intervals (i.e. setting a predetermined value for each of the N angle intervals), and N is an integer greater than or equal to 2. In this case, projection data in each energy only cover a range of 360°/N of the circular track, so this belongs to the category of limited angle reconstruction.

(1) First, the multi-energy CT imaging system operates, and the data processing and control device controls to make the X-ray generation device rotate along the circular track, besides, the X-ray generation device operates in each angle interval pre-divided by the data processing and control device at a voltage pre-set for said angle interval to emit X-rays to irradiate the object to be inspected. Accordingly, the data acquisition system consisting of the detector, reading circuit, acquisition triggering signal circuit and data transmission circuit is used for data acquisition, thus projection data in different energies $E_1, E_2, \ldots, E_n$ (n being an integer greater than or equal to 2) are obtained, then operations like background correction, inconsistency correction and negative logarithmic computation are performed to projection data in different energies $E_1, E_2, \ldots, E_n$ so as to obtain line integral data $P_1, P_2, \ldots, P_n$ of the object in energies $E_1, E_2, \ldots, E_n$.

The line integral data $P_1, P_2, \ldots, P_n$ in all energies $E_1, E_2, \ldots, E_n$ are spliced one by one to obtain a complete line integral data covering 360° of the circular track of the X-ray generation device. Next, reconstruction is performed using such methods as common circular track filtering back projection algorithm so as to obtain a hybrid reconstruction result $f_0$. In addition, with respect to the hybrid reconstruction result $f_0$, the structure information in different energies are different, i.e. $f_0$ is an intermediate result of mixing multiple incomplete information together, so it does not have any strict physical meaning Besides, although the line integral data obtained by splicing is discontinuous in angle direction, it is continuous in filtering direction, so the result obtained by back projection can accurately reflect the geometrical structure information of the object (object under inspection).

Figure 5:
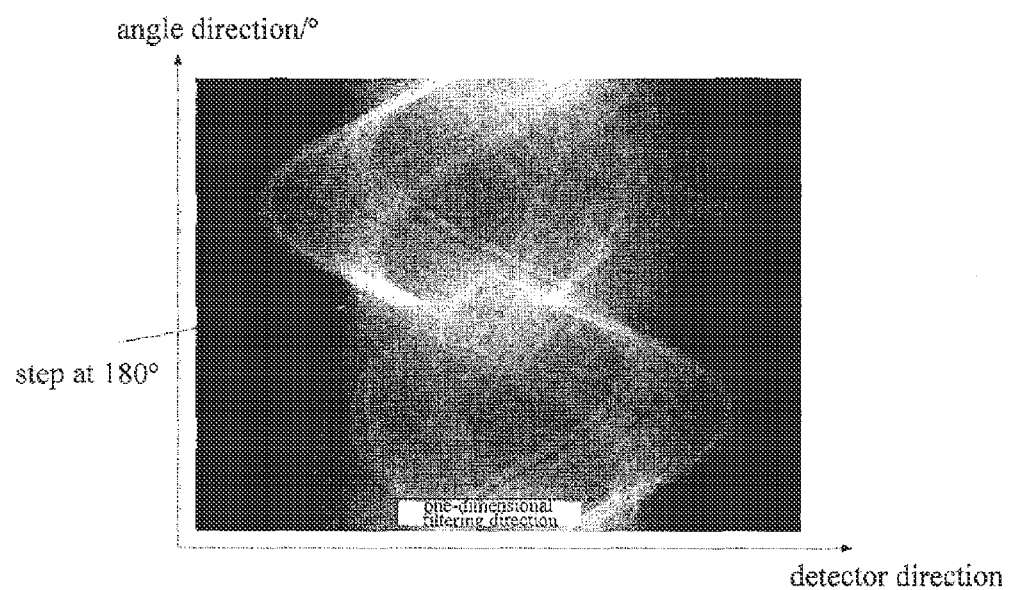
FIG. 5 is a sine map obtained using the dual-energy scan of the present invention.
Figure 6:
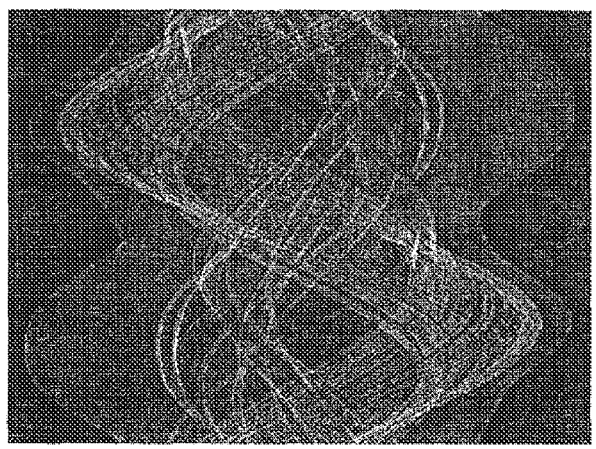
FIG. 6 is a result obtained by convoluting FIG. 5.

In addition, to facilitate understanding, illustrations are made by using two-dimension as an example as shown in FIG. 5. In the example shown in FIG. 5, the circular track is divided into the two angle intervals of 0°~180° and 180°~360° (i.e. dual-energy scan). Here, the result obtained by splicing refers to the sine map usually mentioned in CT. As for said splicing, it means that data (line integral data $P_1$, $P_2, \ldots, P_n$) are put together in angle sequence according to the data formation method of single energy CT despite the difference in energy, so it can be seen in FIG. 5 that energy is switched at 180°, and there is an obvious jumping edge at the place of energy change (i.e. an obvious discontinuity appears at the place of 180°). That is, data are discontinuous in the angle direction (vertical axis in FIG. 5). On the other hand, although energies in these two angle intervals are different, each part includes the structure information of the irradiated object (object under inspection). In addition, since the filtering is a one-dimensional filtering in the detector direction, i.e. performing one-dimensional convolution independently to the line integral data of FIG. 5 row by row, so a step of 180° will not influence the convolution effect, and the result of convolution is shown in FIG. 6.

(2) In order to reconstruct the attenuation coefficients in each of the energies $E_1, E_2, \ldots, E_n$ in a limited range of angles, the hybrid reconstruction result $f_0$ obtained in the above-mentioned way is used as a priori image. The so-called priori image refers to an image that is associated in some way with the image to be reconstructed and that can reflect some information (e.g. structure, edge, feature) of the image to be reconstructed. In the present invention, the priori image refers to the image reconstructed from the line integral data of FIG. 5. Moreover, since the line integral data is obtained by splicing data of different energies, the result of reconstruction is not completely equal to the equivalent attenuation coefficient in any energy, but is very close, and it can fully reflect the object information in geometrical structure.

Next, in order to obtain the attenuation coefficient reconstruction result $f_i$ (i=1, 2, . . . ,n) in each of the energies $E_1$, $E_2, \ldots, E_n$), an optimization problem arg min $G(f_i, f_0)$ of priori constraint is constructed, so that $\|H_i f_i - p_i\|_2 < \epsilon$, which means searching for a parameter $f_i$, and making the function $G(f_i, f_0)$ to reach a global minimum while satisfying the condition of $\|H_i f_i - p_i\|_2 < \epsilon$; alternatively, an equivalent description is searching for the $f_i$ that can make $G(f_i, f_0)$ minimum from all variables $f_i$ that satisfy the condition of $\|H_i f_i - p_i\|_2 < \epsilon$. Wherein, $G(x, y)$ is a function describing the difference between the priori image and the reconstruction result, which can be defined, for example, as $G(x,y) = |\nabla^2(x-y)|$ or $G(x, y) = |\text{diag}^{-1}(y)x + \text{diag}^{-1}(x)y - 2|$, etc. $H_i$ is the projection operator in the $i^{th}$ energy and it only includes the part corresponding to the range of angle covered in the $i^{th}$ energy, and $\epsilon$ is a parameter relating to measurement of the data noise variance. In addition, the above problem is transformed into an unconstrained optimization problem $\min G(f_i, f_0) + \lambda \|H_i f_i - p_i\|_2$ using the Lagrange's method of multipliers, and the problem is solved by a nonlinear conjugate gradient method to obtain the attenuation coefficient reconstruction results $f_i$ (i=1, 2, . . . n) in each of the energies $E_1, E_2, \ldots E_n$.

Since the priori image $f_0$ has complete edge and structure information, and the limited angle line integral data include true attenuation coefficient information, by combining them together, accuracy of both the geometrical structure and the attenuation coefficient can be guaranteed.

(3) As described above, attenuation coefficient reconstruction results $f_1, f_2, \ldots f_n$ in different energies $E_1, E_2, \ldots, E_n$ are obtained, then decomposition coefficients can be obtained using a post-processing base effect decomposition method, thereby obtaining the atomic number and electron density.

Usually, in the reconstruction of atomic number and electron density by dual-energy decomposition, $\mu(E)$ represents the linear attenuation coefficient, which can be the attenuation coefficient of a certain energy value E or the equivalent attenuation coefficient obtained when the X-ray machine high voltage is E, depending on different methods. Attenuation of X-rays caused by substances mainly includes photoelectric effect and Comptow effect, which can be decomposed into energy-related photoelectric function and Comptow function (Klein-Nishina equation), as shown in equation (1) below:

$$\mu(E) = \frac{K_1 N_A}{2} f_{ph}(E) Z^{3.5} \rho_e + \frac{K_2 N_A}{2} f_{KN}(E) \rho_e, \quad (1)$$

wherein, $K_1$, $K_2$ are constants, $N_A$ is the Avogadro's number, the photoelectric function $f_{ph}(E)$ and the Comptow function $f_{KN}(E)$ are known functions, and the two decomposition coefficients are $Z^{3.5} \rho_e$ and $\rho_e$. In addition, in the base effect method, the atomic number Z and the electron density $\rho_e$ are obtained by means of the above relation. The pre-processing method is to first obtain the line integral of the decomposition coefficients, and then reconstruct the decomposition coefficient, and finally obtain Z and $\rho_e$, while the post-processing method is to calculate the decomposition coefficient directly from the attenuation coefficient image and then obtain Z and $\rho_e$.

Furthermore, according to the hypothesis of the dual-energy theory, the X-ray attenuation coefficient can also be decomposed into a combination of the linear attenuation coefficients of two kinds of known material, as shown in equation (2) below:

$$\mu(E) = b_1 \mu_1(E) + b_2 \mu_2(E) \quad (2),$$

wherein, $\mu_1(E)$ and $\mu_2(E)$ are functions of the linear attenuation coefficients of known materials, such as carbon and aluminum, or bone and soft tissue. The decomposition method performs pre-processing and post-processing respectively, and after obtaining the decomposition coefficients $b_1$ and $b_2$, Z and $\rho_e$ can be calculated using the equation (3) below:

$$Z = \left[\frac{b_1\rho_{e1}Z_1^{3.5} + b_2\rho_{e2}Z_2^{3.5}}{b_1\rho_{e1} + b_2\rho_{e2}}\right]^{\frac{1}{3.5}} \quad (3)$$

$$\rho_e = b_1\rho_{e1} + b_2\rho_{e2},$$

wherein, $Z_1$, $Z_2$, $\rho_{e1}$, and $\rho_{e2}$ are atomic numbers and electron densities of known decomposition materials.

In the present invention, taking the dual-energy as an example, the post-processing base material decomposition model is as shown in the following equation (4):

$$f_{E_1}(\vec{r}) = c_1(\vec{r})b_1(\overline{E}_1) + c_2(\vec{r})b_2(\overline{E}_1)$$

$$f_{E_2}(\vec{r}) = c_1(\vec{r})b_1(\overline{E}_2) + c_2(\vec{r})b_2(\overline{E}_2) \quad (4),$$

wherein, $b_1$ and $b_2$ are attenuation coefficients of the used two known base materials in high energy equivalent energy and low energy equivalent energy, and the base material decomposition coefficients $c_1$ and $c_2$ can be obtained from the above equation (4). The base material decomposition coefficients $c_1$ and $c_2$ in equation (4) are equivalent to $b_1$ and $b_2$ in the above equation (2), so the atomic number Z and electron density $\rho_e$ can be further obtained from the above equation (3), accordingly, the atomic number distribution image and electron density distribution image can be obtained.

(4) In addition, attenuation coefficient images in different energies $E_1, E_2, \ldots, E_n$ have been reconstructed in the above (2), and by performing orthographic projection to these images, the completed projection data can be obtained, in which the scanning in different angles have been missing. After obtaining the complete projection data, coefficients of different base functions can be obtained by means of pre-processing. Taking the dual-energy as an example in the present invention, the pre-processing base effect decomposition model is the following equation (5):

$$I_{E_1} = \int D_{E_1}(E)e^{-A_1 f_{ph}(E) - A_2 f_{KN}(E)} dE$$

$$I_{E_2} = \int D_{E_2}(E)e^{-A_1 f_{ph}(E) - A_2 f_{KN}(E)} dE \quad (5),$$

wherein, $I_{E_1}$ and $I_{E_2}$ are complete projection data obtained by splicing the directly measured projection values in the dual-energy limited range of angles and the discrete projection values of the reconstructed images, $A_1$ and $A_2$ are the line integrals of the photoelectric effect coefficient and the Comptow effect coefficient, $D_{E_1}$ and $D_{E_2}$ are products of the spectrums of different energies and the detector response function, which are called the equivalent spectrums. From said equation (5), line integrals of two effects can be obtained, and then by means of the conventional FBP algorithm, the photoelectric coefficient and the Comptow coefficient can be obtained from reconstruction, thus the atomic number and electron density can be obtained. Therefore, the atomic number distribution image and electron density distribution image can be obtained.

Specifically, when attenuation coefficient reconstruction results $f_1, f_2, \ldots f_n$ in different energies $E_1, E_2, \ldots, E_n$ have been obtained, projection data in their missing angles are completed in n energies. Here, dividing the circular track into two angle intervals of 0-180° (marked as "the first angle interval") and 180~360° (marked as "the second angle interval") using two energies is taken as an example. Data in the first energy (i.e. energy corresponding to the first angle interval) lack projection data of 180~360°, so said data are completed by projecting and calculating data of 180~360° using the obtained $f_1$, and data in the second energy (i.e. energy corresponding to the second angle interval) lack projection data of 0~180°, so said data are completed by projecting and calculating data of 0~180° using the obtained $f_2$, i.e. the projection data are completed under the condition of scan missing in different angles, and after obtaining the complete projection data, coefficients of different base functions are obtained by means of a pre-processing method.

A base function decomposition is performed to the complete projection data to obtain coefficients corresponding to the base function, i.e. $A_1$ and $A_2$ in equation (5) are results of using the base function according to the photoelectric effect and the Comptow effect. In fact, the attenuation coefficient functions of some materials that vary with the spectrum may also be used as the base functions, i.e. the base material decomposition method in the art. Data obtained from the decomposition are data of the projection domain, and by means of the conventional FBP algorithm, coefficient distribution can be obtained, from which the atomic number distribution and electron density distribution can be calculated.

Generally, the two materials of bone and soft tissue are preferably used in medical applications to perform post-processing and decomposition, in contrast, in security check applications, pre-processing and decomposition of the photoelectric effect and the Comptow effect are preferably used.

As mentioned above, according to the multi-energy CT imaging system and imaging method of the present invention, in the case of dividing the circular track of the X-ray generation device into multiple angle intervals, the atomic number Z and electron density $\rho_e$ of the object to be inspected (object under inspection) can be accurately obtained, thereby obtaining the atomic number distribution image and the electron density distribution image. Moreover, the multi-energy CT imaging system of the present invention does not increase the number of X-ray generation device or detector, so the cost will not increase, but a multi-energy imaging function can be provided. Moreover, unlike the fast energy switching system in the prior art, the present invention does not need any new model X-ray machine, so it can be widely used.

A dual-energy CT imaging system is designed according to the present invention and the following embodiment is given.

For example, the circular track of the X-ray machine is divided into two angle intervals of 0~180° and 180~360°, and the X-ray machine high voltage in the angle interval of 0~180° is set to be 120 KV, and the X-ray machine high voltage in the angle interval of 180~360° is set to be 80 KV.

First, the X-ray machine high voltage in the dual-energy CT imaging system of the present invention is set to be 120 KV and the machine is turned on to scan.

Next, the rack of the dual-energy CT imaging system rotates continuously, and acquires projection data at a sampling interval of 1°.

Then, when the rack rotates 180°, the data processing and control devices sends an instruction to quickly switch the X-ray machine high voltage to 80 KV, and the scan continues and the interval of scan sampling is still 1°.

When the rack returns to its initial position after rotating 360°, it stops rotating and meanwhile the X-ray machine is turned off, and the data acquisition is finished.

Then, the data processing and control device of the dual-energy CT imaging system splices the line integral data obtained under the X-ray machine high voltages 120 KV and 80 KV to obtain complete line integral data covering 360°, besides, a hybrid reconstruction result $f_0$ that is used as the priori image is obtained according to said complete line integral data.

Next, attenuation coefficient reconstruction results $f_1$ and $f_2$ under 120 KV and 80 KV are obtained respectively according to the priori image $f_0$.

Next, the atomic number Z and electron density $\rho_e$ of the object under inspection are obtained according to said reconstruction results $f_1$ and $f_2$, and the atomic number distribution image or electron density distribution image are displayed according to the atomic number Z and electron density $\rho_e$, or the attenuation coefficient images in different energies can be displayed.

According to the invention of the present application, the circular track of the X-ray generation device is divided into pre-set angle intervals without changing the hardware design of the existing conventional single energy CT system, and a predetermined high voltage of the X-ray generation device is set for each angle interval, and a multi-energy imaging function (especially the dual-energy CT function) is provided using the reconstruction method of the present invention; besides, it has a low cost compared to the existing dual-energy CT device.

What is claimed is:

1. A multi-energy CT imaging system comprising:
a stage for carrying an object to be inspected;
a voltage-regulatable X-ray generation device for emitting X-rays for radiating said object to be inspected;
a detector for receiving X-rays emitted from said X-ray generation device and penetrating said object to be inspected, and for outputting detection data;
a rack having said X-ray generation device and said detector mounted thereon; and
a data processing and control device for controlling said stage, said X-ray generation device, said detector and said rack, processing detected data from said detector, and during one rotation of scan of said X-ray generation device, evenly dividing a circular track of said X-ray generation device into angle intervals of a predetermined number according to a predetermined number of energies and setting a different high voltage of said X-ray generation device for each angle interval, and when said rack rotates from the current angle interval into a next angle interval, controlling said X-ray generation device according to an instruction from said data processing and control device to switch said X-ray generation device to a voltage set in the next angle interval.

2. A method for imaging with a multi-energy CT imaging system, comprising:
(a) providing a multi-energy CT imaging system of claim 1;
(b) evenly dividing the circular track of the X-ray generation device of said multi-energy CT imaging system into angle intervals of a predetermined number according to the predetermined number of energy and setting a different high voltage of said X-ray generation device for each angle interval;
(c) rotating said X-ray generation device along the circular track and working in each angle interval at a high voltage set for said angle interval to emit X-rays to irradiate the object to be inspected;
(d) acquiring projection data of different energies using the detector of said multi-energy CT imaging system;
(e) obtaining line integral data of the projection data of said different energies using the data processing and control device of said multi-energy CT imaging system;
(f) splicing said line integral data of different energies one by one to obtain a complete line integral data covering 360°;
(g) reconstructing according to said complete line integral data to obtain a hybrid reconstruction result;
(h) using said hybrid reconstruction result as a priori image to obtain attenuation coefficient reconstruction results in different energies;
(i) obtaining decomposition coefficients from said attenuation coefficient reconstruction results and obtaining an atomic number distribution image and electron density distribution image using said decomposition coefficient.

3. The method of claim 2, wherein the circular track of step (b) is divided into N angle intervals and the line integral data in different energies obtained in step (e) are made to be $P_1$, $P_2$, ... $P_n$, and in step (g), reconstruction is performed using a common circular track filtering back projection method so as to make the obtained hybrid reconstruction result to be $f_0$, N and n being integers greater than or equal to 2;
in step (h), an attenuation coefficient reconstruction result fi that satisfies the condition of $\|H_i f_i - p_i\|_2 < \epsilon$ is obtained by means of arg min $G(f_i, f_0)$, wherein, $G(f_i, f_0)$ is a function describing the difference between the priori image and the reconstruction result, $H_i$, is a projection operator in the $i^{th}$ energy, $\epsilon$ is a parameter related to measurement of data noise variance, i=1, 2, ..., n.

4. The method of claim 3, characterized in that in step (h), a decomposition coefficient is obtained using a post-processing base function decomposition method, then said decomposition coefficient is used to obtain the atomic number distribution image and electron density distribution image.

5. The method of claim 3, characterized in that in step (i), a decomposition coefficient is obtained using a post-processing base material decomposition method, then said decomposition coefficient is used to obtain the atomic number distribution image and electron density distribution image.

6. The method of claim 3, characterized in that in place of said step (i), there is such a step (j) as performing orthographic projection to the attenuation coefficient reconstruction result $f_i$, obtained in step (h) to obtain the completed projection data in which the scanning plane in different angles have been missing, then obtaining coefficients of different base functions by means of pre-processing, thus obtaining the atomic number distribution image and electron density distribution image.

* * * * *

UNITED STATES PATENT AND TRADEMARK OFFICE
CERTIFICATE OF CORRECTION

PATENT NO. : 9,326,743 B2  
APPLICATION NO. : 14/135023  
DATED : May 3, 2016  
INVENTOR(S) : Le et al.

Page 1 of 1

It is certified that error appears in the above-identified patent and that said Letters Patent is hereby corrected as shown below:

In Claim 3, column 12, line 29. An 'i' has been replaced with a 't'.

The Letters Patent reads:

$$\|H_j f_j - p_i\|_2 < \epsilon$$

However, it should read:

$$\|H_i f_i - p_i\|_2 < \varepsilon$$

Signed and Sealed this  
Twenty-eighth Day of June, 2016

Michelle K. Lee  
*Director of the United States Patent and Trademark Office*